United States Patent [19]

Schwartz et al.

[11] Patent Number: 4,851,235

[45] Date of Patent: Jul. 25, 1989

[54] PRODUCTION OF FERMENTED WHEY PRODUCTS CONTAINING AN EMULSIFIER

[75] Inventors: Robert D. Schwartz, Concord; Thomas M. Anderson, Emeryville; Enrique Fernandez, San Bruno, all of Calif.

[73] Assignee: National Starch and Chemical Corporation, Bridgewater, N.J.

[21] Appl. No.: 940,993

[22] Filed: Dec. 12, 1986

[51] Int. Cl.$^4$ .................. A23L 1/035; C12P 19/04; C12R 1/73; C12N 1/16

[52] U.S. Cl. .................................. 426/33; 426/41; 426/62; 426/654; 435/101; 435/255; 435/923

[58] Field of Search .............. 426/41, 654, 33, 62; 435/101, 255, 923

[56] References Cited

U.S. PATENT DOCUMENTS

| | | | |
|---|---|---|---|
| 3,616,234 | 10/1971 | Komagata | 435/923 |
| 3,966,554 | 6/1976 | Vass et al. | 426/56 |
| 3,973,042 | 8/1976 | Kosikowski et al. | 426/61 |
| 4,001,437 | 1/1977 | Jaeggi et al. | 426/41 |
| 4,039,687 | 8/1977 | Weyn | 426/62 |
| 4,141,791 | 2/1979 | Martini et al. | 426/63 |
| 4,178,391 | 12/1979 | Chao et al. | 426/61 |
| 4,361,588 | 11/1982 | Herz | 426/583 |
| 4,670,267 | 6/1987 | Chang et al. | 426/41 |
| 4,675,193 | 6/1987 | Boudreaux | 426/41 |

FOREIGN PATENT DOCUMENTS 1059889  2/1967  United Kingdom ............... 435/923

OTHER PUBLICATIONS

*Candida lipolytica* Applied & Envir. Microbiol., Oct. 1984, pp. 747–750, vol. 48, #4.

Biotech 85-12771 Cirigliano et al. AEMIDF (1985) vol. 50, #4, pp. 846–850.

Biotech. 85-04984 Cirigliano et al., Abs. "Annual Meeting Am. Soc. Microbiol.", (1985) 85 Meet 237.

*Primary Examiner*—Herbert J. Lilling
*Attorney, Agent, or Firm*—Royal N. Ronning, Jr.; Edwin M. Szàla

[57] ABSTRACT

Dairy whey, a waste product of cheese production, is fermented with an organism to produce a whey product containing an emulsifier. Fermentation is carried out by forming a fermentation broth of whey or whey and oil, and optionally yeast extract and then fermenting the broth with *Candida lipolytica*. The resultant fermented whey product is used as an emulsifying agent in the food industry.

7 Claims, No Drawings

PRODUCTION OF FERMENTED WHEY PRODUCTS CONTAINING AN EMULSIFIER

FIELD OF THE INVENTION

This invention relates to a method of producing food grade and cosmetic grade emulsifier containing broths by fermention processes.

BACKGROUND OF THE INVENTION

Controlled fermentation of food can be used as a means of improving functionality of food. Diary whey and vegetable oils are foods which may be an economical source of fermentable substrates. They are widely used as ingredients in manufactured foods. If whey or whey and vegetable oil can be functionalized by fermentation with an organism that produces an emulsifier when grown on these substrates, it is possible to obtain products that may serve the function of an emulsifier or emulsion stabilizer.

Whey is the fluid medium containing a very low concentration of milk solids and a high concentration of lactose. Disposal of this waste by-product by drying is an energy-intensive, expensive procedure which results in an expensive by-product. Sewering of the whey is prohibitive in cost due to the high biological oxygen demand which is placed on municipal sewer systems.

Vegetable oils are extracted and refined products derived from various plants such as corn, soybeans, and sunflower plants for example. These oils are consumed as foods themselves or as constituents of other prepared foods.

The most desirable method of handling a whey waste stream is to produce a high quality natural food ingredient from the whey waste product. Applicant has discovered a novel method of producing a functionalized whey product or the whey product plus vegetable oils for use as a food ingredient or any type of product where milk solids, lactose or vegetable oils are acceptable ingredients.

BRIEF DESCRIPTION OF THE INVENTION

The process of this invention provides a method of functionalizing whey or whey and vegetable oil by forming a fermentation broth of the whey or whey and vegetable oil and optionally yeast extract and then fermenting the broth with the organism Candida lipolytica.

DETAILED DESCRIPTION OF THE INVENTION

A functionalized dairy whey product or dairy whey plus vegetable oil having the ability to increase the emulsification capacity or increase the emulsion stability or decrease the surface tension of an oil and water emulsion for use as a food or cosmetic ingredient that may serve as a stabilizer, thickener, or emulsifier, can be produced by fermenting a mixture comprising whey or whey plus vegetable oil and optionally, yeast extract with the organism Candida lipolytica to produce a functionalized produce containing an emulsifier produced by the organism Candida lipolytica.

Any organism that can produce an emulsifier, stabilizer or thickener on the substrate can be useful in the fermentation. The preferred microorganism is Candida lipolytica ATCC 20324.

Fermentation of a whey broth comprising unhydrolyzed whey (acid or sweet), or unhydrolyzed whey and vegetable oil, and optionally yeast extract results in stabilizer, thickener or emulsifier formation and functionalization of the whey so that the whey produce can be utilized as a food ingredient. This aerobic fermentation can be carried out preferably in a pH range of 5 to 8, most preferably with the pH maintained in a range from about 5.5 to about 6.5. The fermentation can be carried out at a temperature from about 20° to 35° C., most preferably carried out at a temperature from about 25° to about 30° C.

The term "whey" is meant to include whole whey and reconstituted wheys of up to 18% solids and ultrafiltered whey referred to as "whey permeate".

Typical composition of Teklac (sweet dairy whey) is as follows:

| CHEMICAL AND PHYSICAL SPECIFICATIONS | |
|---|---|
| Ingredient | |
| Listing: Whey | |
| Typical Proximate Analysis | |
| Protein (N × 6.38)% | 12.7 |
| Fat % | 1.1 (1.25% Maximum) |
| Moisture % | 4.5 (5.0% Maximum) |
| Ash % | 8.0 |
| Lactose % | 71.3 |
| Calories, Cal/100 g | 350.0 |
| Typical Vitamin & Mineral Analysis | |
| Vitamin A I.U./100 g | Nil |
| Vitamin C mg/100 g | Nil |
| Thiamin mg/100 g | 0.40 |
| Riboflavin mg/100 g | 1.76 |
| Niacin mg/100 g | 1.00 |
| Calcium % | 0.71 |
| Iron % | Nil |
| Vitamin $B_{12}$ μg/100 g | 2.12 |
| Phosphorus % | 0.69 |
| Pantothenic Acid mg/100 g | 4.09 |
| Microbiological Standards | |
| Standard Plate Count | 10,000/g (Maximum) |
| Coliforms | 9/g (Maximum) |
| E. coli | Negative |
| Salmonella | Negative |

The nutritional values listed above are within 80% of the value declared in compliance with Federal Nutritional Regulations 21 CFR S1.17(4)(ii).

| Typical Range | | Limit | |
|---|---|---|---|
| Solubility Index | 0.1–0.5 ml | 1.25 ml | Max. |
| Acidity | 0.10–0.14% | 0.16 | Max. |
| Alkalinity of Ash | 175–200 ml | 225 ml | Max. |
| Scorched Particles | 7.5 mg | 15.0 mg | Max. |
| Particle size (Through 40 Mesh) | 99–100% | 98% | Min. |

In the fermentation broth concentration of whey solids can range from about 0.5% to about 18.0%, preferably from about 1% to about 3%, and the concentration of vegetable oil when used can range from about 1.0% to about 10.0%, preferably 2% to 5%. The additional yeast extract in the fermentation broth can range from about 0.01% to a about 2.0%, preferably from about 0.05% to about 1.0%. Adequate fermetation broth surface tensions of below about 4 mN/m (milliNewtons per meter) are usually reached within 18 to 36 hours. All of the above weight percents are in weight per volume.

Any vegetable oils can be used but the preferred oils are those derived from corn, soybean and sunflower.

By the term "surface tension" is meant the force (tension) of a liquid which makes the surface act as an elastic enveloping membrane which always tends to contract to the minimum are. It is expressed as the work required to increase the surface area by one unit and is usually given as milliNewtons per meter (mN/m).

By the term "emulsification capacity" is meant the amount of oil which can be emulsified without phase inversion by a given amount of emulsifier. The procedure for testing emulsification capacity is as follows:
  (a) add to a 250 ml stainless steel beaker 20 ml of aqueous solution;
  (b) place OHM meter probes inside the beaker as far apart as possible without touching the side of the beaker;
  (c) measure the initial resistance;
  (d) add oil while the solution is being mixed with a T-line lab stirrer;
  (e) stop the oil addition when infinite resistance is observed on the meter; and
  (f) record the volume of oil added.

"Infinite resistance" indicates a phase inversion from an oil/water emulsion (wherein the continuous phase is water) to a water/oil emulsion (where the continuous phase is oil). The more oil required to achieve this inversion the greater the capacity of the emulsifier.

The term "emulsion stability" defines the resistance of an emulsion to phase separation. This resistance is tested by the following procedure:
  (a) to a test tube add a fixed volume of water with the emulsifier dispersed in it;
  (b) measure the height of the water column in centimeters (cm);
  (c) add a fixed volume of oil and measure the height of the oil in the column in cm;
  (d) vortex for 20 s on high setting; and
  (e) measure the water or oil separation in cm vs. time.

The stability is calculated (in %) as the amount of water separated after 60 minutes relative to the amount of water initially present:

$$\% = \frac{(\text{cm H}_2\text{O present after } 60')(100)}{\text{cm H}_2\text{O initially present}}$$

The lower the percentage, the more stable the emulsion.

Emulsion Type. To determine if an emulsion is of the oil/water or water/oil type, the following procedure is used:
  (a) to a Petri dish add 10 ml water;
  (b) to another Petri dish add ml oil;
  (c) with a disposable pipette add one drop of emulsion to the water and add another drop to the oil.

If the drop disperses (breaks up) in the oil, it indicates that the oil is the continuous phase and the emulsion is of the water/oil type. If the drop disperses in the water, it indicates the emulsion is of the oil/water type.

EXAMPLE 1

*Candida lipolytica* ATCC 20324 was grown in baffled 500 milliliter (ml) shake flasks containing 100 ml of 2% Teklac and 1% yeast extract. The medium was sterilized by autoclaving for 20 minutes at 121° C. at 15 psig. Flasks were incubated at 30° C., 250 rpm on a rotary shaker for 24 hours. Optical density was determined by diluting culture 1/50 in deionized water and measuring absorbance at 535 nm. Viable counts were determined by spread plating on YM agar and incubating as described above.

Broth samples were diluted 1/20 for the emulsification assays. The emulsion capacity was determined by the amount of oil (mL) required to invert the emulsion from oil/water to water/oil when added to 20ml of aqueous phase, i.e., fermented broth. The emulsion stability was determined by the percent of water separated from the emulsion at the point of inversion after one hour. The stability is expressed as percent separation, thus lower values indicate high stability. Uninoculated media were used as controls.

Table I shows typical emulsification results for inoculated broth and uninoculated control broth.

TABLE 1

Growth and Emulsification Properties of *C. lipolytica* in Whey-Based Media

| Broth | Growth pH | OD | TVC/mL | Emulsification Assay Capacity (ml) | Stability (%) |
|---|---|---|---|---|---|
| unfermented broth control | 6.6 | — | | 85 | 62 |
| fermented broth with *C. lipolytica* | 8.4 | 4.5 | 9.4 × 10$^7$ | 192 | 53 |
| fermented broth adjusted to pH 7.0 | 7.0 | | | 158 | 45 |

The culture grown in T2Y1 demonstrated a greater than two-fold increase in emulsion capacity and a significant increase in stability (decrease in phase separation) compared to the medium control. When the sample was adjusted to pH 7.0, there was a decrease in emulsification capacity, but it was still almost twice the broth control.

EXAMPLE 2

*Candida lipolytica* ATCC 20324 was grown in baffled 500 ml shake flasks containing 100 ml of 2% Teklac, 1% yeast extract and either 2% or 10% corn oil. The whey broth containing yeast extract was sterilized by autoclaving as defined in Example 1. The corn oil was also sterilized by autoclaving as defined in Example 1 and added to the whey broth at the time of use. Flasks were incubated at 30° C., 250 rpm on a rotary shaker for 72 hours. Samples were aseptically withdrawn periodically and the pH and surface tension determined.

Surface tension was measured on a Fisher Autotensiomat ® Model 215. Where indicated, broths were appropriately diluted in 0.02 M Tris ® plus 10mM MgSO$_4$ buffer, pH 7.2. The surface tension of this buffer is 68-72 mN/m.

The greatest broth dilution at which the minimum surface tension is reached is the critical micelle dilution (CMD), expressed as the reciprocal of the dilution. At the CMD, surfactant molecules free in solution come into equilibrium with micelles and the concentration of free molecules becomes constant, regardless of increasing total surfactant concentration. Thus, further increases in surfactant concentration do not result in further reductions in surface tension. The greater the dilution at which this occurs the greater the concentration of the surfactant, i.e., the more surfactant produced in the fermentation.

Results are shown in Table 2 for inoculated and uninoculated media.

TABLE 2

| Medium Time, hour | Inoculated | | | | Uninoculated Control | | | |
|---|---|---|---|---|---|---|---|---|
| | Broth pH | Surfactant Activity | | | Broth pH | Surfactant Activity | | |
| | | ST[1] @ CMD | CMD[2] | pH @ CMD[2] | | ST[1] @ CMD | CMD[2] | pH @ CMD |
| T2Y1[3] + 2% oil | | | | | | | | |
| 0 | 6.8 | 44 | 0 | 6.8 | 6.6 | 44 | 0 | 6.6 |
| 24 | 5.6 | 29 | 2 | 7.0 | 6.7 | 46 | 0 | 6.7 |
| 48 | 5.0 | 38 | 1 | 6.3 | 6.6 | 46 | 0 | 6.7 |
| 72 | 7.1 | 48 | 0 | 7.1 | 6.7 | 46 | 0 | 6.7 |
| T2Y1 + 10% oil | | | | | | | | |
| 0 | 6.8 | 44 | 0 | 6.8 | 6.6 | 44 | 0 | 6.6 |
| 24 | 5.6 | 29 | 4 | 7.1 | 6.7 | 42 | 0 | 6.7 |
| 48 | 5.3 | 29 | 3 | 7.1 | 6.7 | 46 | 0 | 6.7 |
| 72 | 5.4 | 29 | 3 | 7.3 | 6.8 | 46 | 0 | 6.8 |

Reduction in Surface Tension (ST) by *C. lipolytica* Growing in Various Media

[1] = mN/m
[2] = 0 Dil = Undiluted broth, $1 = 10^{-1}$, $2 = 10^{-2}$, etc.
[3] = T2Y1 is 2% Teklac and 1% yeast extract.

At oil concentrations of 2% and 10%, the greatest CMD occurred after 24 hours of incubation. The CMD was 100 fold and 10,000 fold greater in 2% oil and 10% oil, respectively, compared to the uninoculated controls. The surface tension was also lower than in the uninoculated controls.

The surface active broths produced by fermentation techniques of this invention may be concentrated by partial drying, dried or pasteurized and/or dried by lyophilization, spray drying, and other techniques.

The functionalized whey product of this invention can be used as a food or cosmetic ingredient where milk solids and/or whey, and/or vegetable oils, and/or thickeners, and/or emulsifiers, and/or stabilizers are used such as in ice cream, baked goods, salad dressings, foam stabilizers (meringue), puddings, snack foods, hand lotions, shampoos, make-up, etc.

The term "emulsifier" means a substance which makes an emulsion more stable by reducing the surface tension or protecting the droplets with a film.

The term "emulsion" means a fluid consisting of a microscopically heterogenous mixture of two normally immiscible liquid phases, in which one liquid forms minute droplets suspended in the other liquid.

The term "stabilizer" means a substance added to a solution to render it more stable.

The term "thickener" means a substance which when mixed with a fluid increases the viscosity of the fluid.

The term "functionalizing" means to impart a new function to a fermentable substrate material by the action of a microorganism. The entire fermentation broth, including the microorganism, is utilized without seperation for the purpose of the new function as a naturally produced material exhibiting the function.

What is claimed:

1. A process for producing an emulsifier containing functionalized dairy whey product comprising the steps of:
   (a) forming a fermentation broth of unhydrolyzed whey or whey and from about 2.0% to about 10.0% by wt/vol of vegetable oil; and
   (b) fermenting the broth with the organism *Candida lipolytica* at a pH of at least 5.5 and at a time and temperature sufficient to produce a functionalized diary whey product containing an emulsifier produced by the organism.

2. The process of claim 1 wherein the fermentation broth also contains yeast extract.

3. The process of claim 1 wherein the whey concentration ranges from about 0.5% to about 18.0% by wt/vol.

4. The process of claim 1 wherein the whey concentration ranges from about 2.0% to about 5.0% by wt/vol.

5. A functionalized dairy whey having emulsification properties comprising a fermented dairy whey produced by the process of:
   (a) forming a fermentation broth of unhydrolyzed whey or whey and from about 2.0% to about 10.0% by wt/vol of vegetable oil; and
   (b) fermenting the broth with the organism *Candida lipolytica* at a pH of at least 5.5 and at a time and temperature sufficient to produce a functionalized dairy whey product containing an emulsifier produced by the organism.

6. The concentrated product of claim 5.

7. The dried product of claim 5.

* * * * *